US011123519B2

(12) United States Patent
Beeckler

(10) Patent No.: US 11,123,519 B2
(45) Date of Patent: Sep. 21, 2021

(54) LAYERED TUBE FOR IMPROVED KINK RESISTANCE

(71) Applicant: Biosense Webster (Israel) Ltd., Yokneam (IL)

(72) Inventor: Christopher Thomas Beeckler, Brea, CA (US)

(73) Assignee: BIOSENSE WEBSTER (ISRAEL) LTD., Yokneam (IL)

(*) Notice: Subject to any disclaimer, the term of this patent is extended or adjusted under 35 U.S.C. 154(b) by 0 days.

(21) Appl. No.: 15/386,461

(22) Filed: Dec. 21, 2016

(65) Prior Publication Data

US 2018/0169380 A1 Jun. 21, 2018

(51) Int. Cl.
*A61M 25/00* (2006.01)
*B29C 48/10* (2019.01)
(Continued)

(52) U.S. Cl.
CPC ......... *A61M 25/0045* (2013.01); *A61L 29/02* (2013.01); *A61L 29/085* (2013.01); *A61M 25/005* (2013.01); *A61M 25/0009* (2013.01); *A61M 25/0141* (2013.01); *B29C 39/18* (2013.01); *B29C 48/10* (2019.02); *B29C 48/151* (2019.02); *B29C 48/154* (2019.02); *B29C 48/21* (2019.02); *B29C 48/23* (2019.02); *A61L 2420/08* (2013.01); *A61M 2025/0047* (2013.01); *A61M 2025/0048* (2013.01); *B29C 48/08* (2019.02); *B29C 48/09* (2019.02);
(Continued)

(58) Field of Classification Search
CPC .......... A61M 25/0045; A61M 25/0049; A61M 25/0054; A61M 2025/0059; A61M 2025/0062; B29C 47/0026; B29C 47/068; B29C 47/0021; B29C 47/0023; B29C 48/151; B29C 48/18; B29C 39/146; B29L 2031/7542; B29L 2023/005
See application file for complete search history.

(56) References Cited

U.S. PATENT DOCUMENTS 5,064,491 A * 11/1991 Huvey .................... B29C 53/12
156/173
5,100,381 A * 3/1992 Burns .................. A61M 25/104
604/103
(Continued)

FOREIGN PATENT DOCUMENTS

CA 2489697 A1 8/1995
CN 103997981 A 8/2014
(Continued)

OTHER PUBLICATIONS

Extended European Search Report for European Application No. EP17209701, dated May 16, 2018; 8 pages.

*Primary Examiner* — Nilay J Shah
(74) *Attorney, Agent, or Firm* — Etan S. Chatlynne; Roberts Calderon Safran & Cole P.C.

(57) ABSTRACT

A catheter shaft is produced by forming a first polymeric layer onto a flexible inner core while maintaining the inner core in a solid state, and solidifying the first polymeric layer, wherein the solidified first polymeric layer fails to bond with the inner core and is slidable thereon upon flexion of the shaft. A second polymeric layer may be formed over the first polymeric layer, and is slidable thereon when the shaft bends.

9 Claims, 2 Drawing Sheets

(51) Int. Cl.

| | |
|---|---|
| *B29C 48/151* | (2019.01) |
| *A61M 25/01* | (2006.01) |
| *B29C 48/154* | (2019.01) |
| *B29C 48/21* | (2019.01) |
| *B29C 48/23* | (2019.01) |
| *A61L 29/02* | (2006.01) |
| *A61L 29/08* | (2006.01) |
| *B29C 39/18* | (2006.01) |
| *B29L 31/00* | (2006.01) |
| *B29C 48/09* | (2019.01) |
| *B29C 48/08* | (2019.01) |
| *B29K 23/00* | (2006.01) |
| *B29K 77/00* | (2006.01) |
| *B29K 79/00* | (2006.01) |

(52) U.S. Cl.
CPC .. *B29K 2023/0683* (2013.01); *B29K 2077/00* (2013.01); *B29K 2079/08* (2013.01); *B29L 2031/7542* (2013.01)

(56) References Cited

U.S. PATENT DOCUMENTS

| | | | |
|---|---|---|---|
| 5,993,462 A | 11/1999 | Pomeranz et al. | |
| 6,019,736 A * | 2/2000 | Avellanet | A61M 25/09 |
| | | | 600/585 |
| 6,464,683 B1 | 10/2002 | Samuelson et al. | |
| 6,692,511 B2 | 2/2004 | Tiernan | |
| 6,837,890 B1 * | 1/2005 | Chludzinski | A61L 29/041 |
| | | | 606/108 |
| 7,556,634 B2 | 7/2009 | Lee et al. | |
| 8,048,352 B2 | 11/2011 | Devens et al. | |
| 8,308,711 B2 | 11/2012 | Lee et al. | |
| 8,353,867 B2 | 1/2013 | Olson | |
| 9,040,136 B2 * | 5/2015 | Procida | B32B 1/08 |
| | | | 428/34.1 |
| 9,089,669 B2 | 7/2015 | Haslinger et al. | |
| 2004/0225278 A1 * | 11/2004 | Poole | A61M 25/0009 |
| | | | 604/523 |
| 2005/0149104 A1 * | 7/2005 | Leeflang | A61B 17/3439 |
| | | | 606/198 |
| 2007/0074805 A1 | 4/2007 | Leeflang et al. | |
| 2009/0312832 A1 * | 12/2009 | Delap | A61F 2/95 |
| | | | 623/1.11 |
| 2013/0048131 A1 * | 2/2013 | Smillie | B32B 27/308 |
| | | | 138/97 |
| 2014/0074083 A1 | 3/2014 | Horn et al. | |
| 2014/0123463 A1 | 5/2014 | Haslinger | |
| 2014/0371676 A1 | 12/2014 | Leeflang et al. | |
| 2016/0296133 A1 | 10/2016 | Osypka et al. | |

FOREIGN PATENT DOCUMENTS

| | | |
|---|---|---|
| EP | 1207930 B1 | 6/2005 |
| EP | 2842525 A1 | 3/2015 |

* cited by examiner

LAYERED TUBE FOR IMPROVED KINK RESISTANCE

COPYRIGHT NOTICE

A portion of the disclosure of this patent document contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF THE INVENTION

1. Field of the Invention

This invention relates to instruments for performing medical examinations of the interior of cavities or tubes of the body. More particularly, this invention relates to a medical catheter constructed by a process for applying fluent materials to a surface or part of a surface.

2. Description of the Related Art

It is common to map and ablate endocardial tissue in subjects having electrical conduction abnormalities. The procedures are performed with an elongate catheter having a lumen extending longitudinally through it. One technique, described in U.S. Pat. No. 5,993,462, involves inserting a core wire into a catheter via the lumen. The core wire includes a pre-shaped region. Such catheters includes a proximal section that is sufficiently rigid to straighten the core wire when the core wire is disposed within the proximal section. A distal section of the catheter is significantly more flexible than the proximal section.

Deflectable catheters are widely used for a variety of applications. In the area of electrophysiology. However, due to their inherent flexibility and limited kink resistance, catheters can be difficult to control as precisely as would be desired. Conventional approaches to increasing kink resistance include: increasing wall thickness, reinforcing the wall with a coil, replacing a large open lumen with a multi-lumen arrangement, or changing the material so that it can stretch and bend more easily.

SUMMARY OF THE INVENTION

According to disclosed embodiments of the invention, a catheter shaft is constructed using multiple film-cast, extruded or coextruded layers of materials that do not chemically bond together. The layers are in extremely good mechanical contact, but when the construction is bent, they are able to slip with respect to each other, which makes the tube more resistant to kinking.

There is provided according to embodiments of the invention a method of making a catheter shaft, which is carried out by forming a first polymeric layer onto a flexible inner core while maintaining the inner core in a solid state, and solidifying the first polymeric layer, wherein the solidified first polymeric layer fails to bond with the inner core and is slidable thereon upon flexion of the inner core.

According to one aspect of the invention wherein forming the first polymeric layer is extruded.

According to yet another aspect of the method, the first polymeric layer is film cast.

A further aspect of the method is carried out by forming a second polymeric layer onto the solidified polymeric first layer, and solidifying the second polymeric layer, wherein the solidified second polymeric layer fails to bond with the solidified first polymeric layer and is slidable thereon upon flexion of the inner core.

According to an additional aspect of the method, the second polymeric layer is extruded.

According to still another aspect of the method, the second polymeric is film cast.

According to yet another aspect of the method, a kinetic coefficient of friction between the solidified first polymeric layer and the solidified second polymeric layer does not exceed 0.5.

According to still another aspect of the method the solidified first polymeric layer and the solidified second polymeric layer are composed of identical materials.

According to an additional aspect of the method, the solidified first polymeric layer and the solidified second polymeric layer are composed of polyimide.

According to a further aspect of the method the solidified first polymeric layer and the solidified second polymeric layer are composed of different materials.

According to another aspect of the method, one of the solidified first polymeric layer and the solidified second polymeric layer is ultra-high-molecular-weight polyethylene and another of the solidified first polymeric layer and the solidified second polymeric layer is polyether block amide.

According to one aspect of the method, the inner core includes a metallic braid.

There is further provided according to embodiments of the invention a catheter shaft having a flexible inner core, a first polymeric layer formed onto the flexible inner core, and a second polymeric layer onto the first polymeric layer, wherein upon flexion of the flexible inner core the first polymeric layer is slidable on the flexible inner core and on the second polymeric layer.

BRIEF DESCRIPTION OF THE SEVERAL VIEWS OF THE DRAWINGS

For a better understanding of the present invention, reference is made to the detailed description of the invention, by way of example, which is to be read in conjunction with the following drawings, wherein like elements are given like reference numerals, and wherein.

DETAILED DESCRIPTION OF THE INVENTION

In the following description, numerous specific details are set forth in order to provide a thorough understanding of the various principles of the present invention. It will be apparent to one skilled in the art, however, that not all these details are necessarily needed for practicing the present invention. In this instance, well-known circuits, control logic, and the details of computer program instructions for conventional algorithms and processes have not been shown in detail in order not to obscure the general concepts unnecessarily.

Documents incorporated by reference herein are to be considered an integral part of the application except that, to the extent that any terms are defined in these incorporated documents in a manner that conflicts with definitions made explicitly or implicitly in the present specification, only the definitions in the present specification should be considered.

Figure 1:
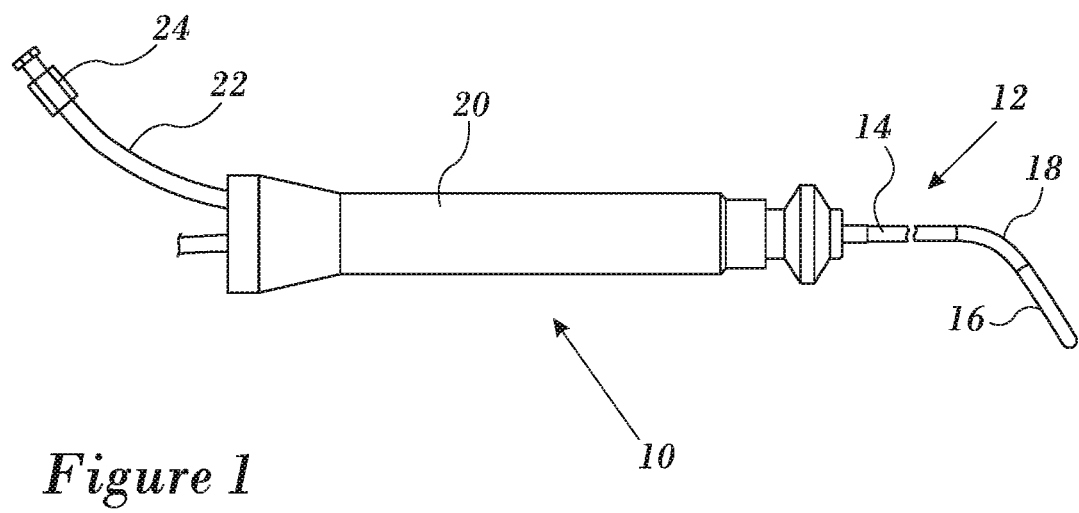
FIG. 1 is a schematic diagram of a medical catheter according to an embodiment of the invention.

Turning now to the drawings, reference is initially made to FIG. 1, which is a schematic diagram of a medical catheter 10 according to an embodiment of the invention. The catheter 10 comprises an elongated shaft 12 having a relatively stiff proximal section 14, relatively flexible distal section 16 with respect to the proximal section 14 and an intermediate section 18. One or more electrodes or other devices are mounted on the distal section 16 for performing mapping, ablation or another desired function, and a control handle 20 is located at the proximal section 14 of the shaft 12. An infusion tube 22 is provided to introduce fluid through a lumen (not shown) of the shaft 12. A leer hub 24 is mounted on the proximal end of the infusion tube 22 to facilitate introduction of the fluid into the catheter 10.

Figure 2:
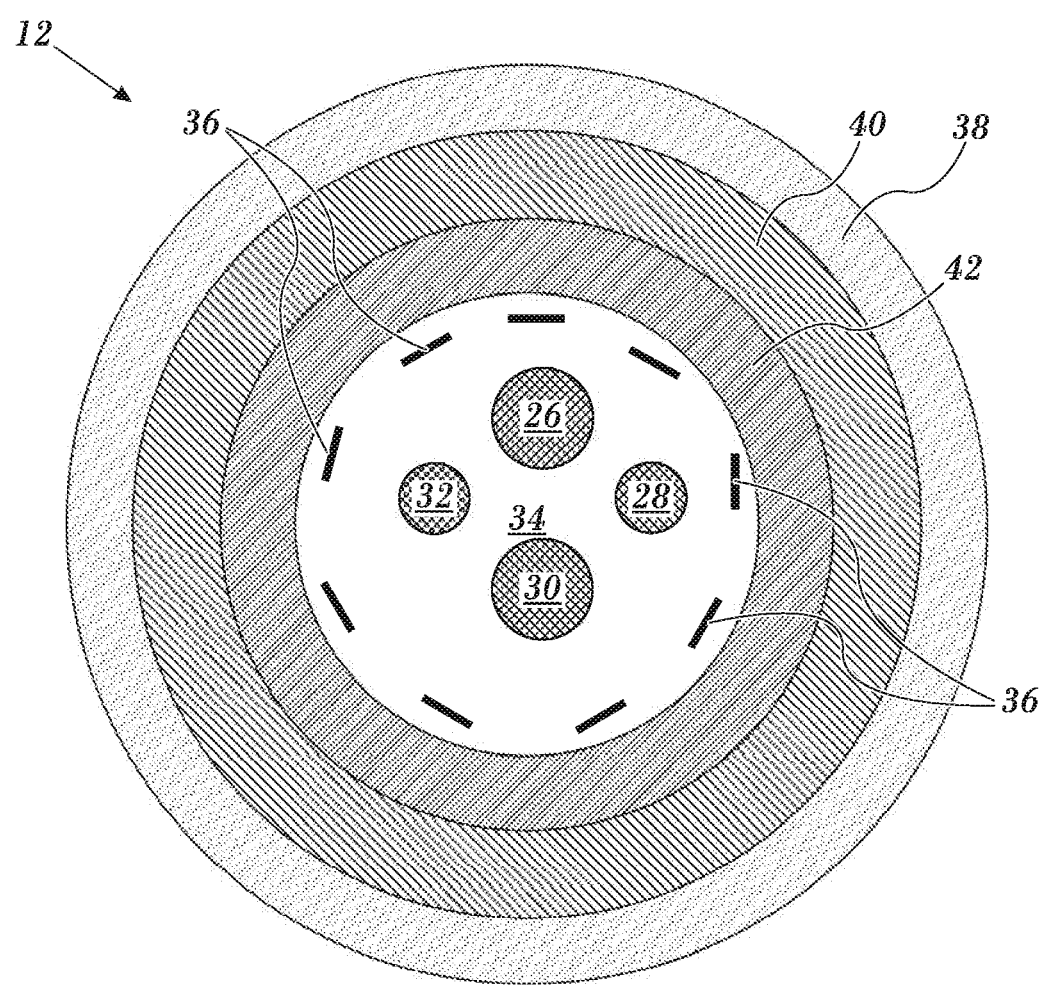
FIG. 2 is a cross sectional view of the shaft of the catheter shown in FIG. 1 in accordance with an embodiment of the invention.

Reference is now made to FIG. 2, which is a cross sectional view of the shaft 12 (FIG. 1) in accordance with an embodiment of the invention. The shaft is constructed by extrusion or coextrusion of thermoplastic materials, as described in the detailed description below. In the depicted embodiment, the shaft 12 includes lumens 26, 28, 30, 32 surrounded by a relatively soft inner extrusion 34, which is drawn through a metallic braid 36. While 4 lumens are shown, a catheter may comprise more or fewer lumens, depending on the application intended.

The inner extrusion 34 and braid 36 are surrounded by a series of layers. Respective outer, middle, and inner layers 38, 40, 42 are shown in the example of FIG. 2; however, the shaft 12 may be constructed with more or fewer layers. The layers may be applied in successive extrusion operations using conventional screw extruders, preferably having barrel cooling systems to obtain good mixing efficiency and melt uniformity, and to avoid surge effects. Dealing with these issues is well known in the extrusion art, and is not dealt with further herein. Alternatively, the layers may be coextruded with the inner extrusion 34.

It is important that the layers 38, 40, 42 and the inner extrusion 34 do not bond to one another, although they are in close physical proximity; indeed in "contact with one another. This requirement enables the layers 38, 40, 42 and the inner extrusion 34 to slide upon one another when the shaft flexes. The layers 38, 40, 42 may be constructed of the same material, e.g., polyimide or a thermoplastic such as polyethylene terephthalate (PET), Pebax®, Polyurethane," or Nylon™. If a thermoplastic is used, layers can be prevented from bonding to one another by keeping each successive inner layer below the melt point of a currently extruding outer layer. When identical materials are used bonding can be avoided if the inner layer is cold and the outer extrusion is put on with at a temperature that is barely high enough for the material to flow. In that case as soon as the outer extrusion touches the inner layer it cools immediately and does not melt into the inner core and form a bond. When film casting is used with polyimide, if the inner layer is solidified it does not make a bond with the outer layer.

Alternatively, the shaft 12 may be built up by alternating layers of different materials that do not bond to each other, for example, ultra-high-molecular-weight polyethylene (UHMWPE) and a polyether block amide, such as Pebax.

Regardless of the materials chosen, it is desirable that there be a low kinetic coefficient of friction between adjacent layers 38, 40, 42 and also between the layer 38 and the inner extrusion 34. A coefficient of friction of 0.5 is satisfactory.

Figure 3:
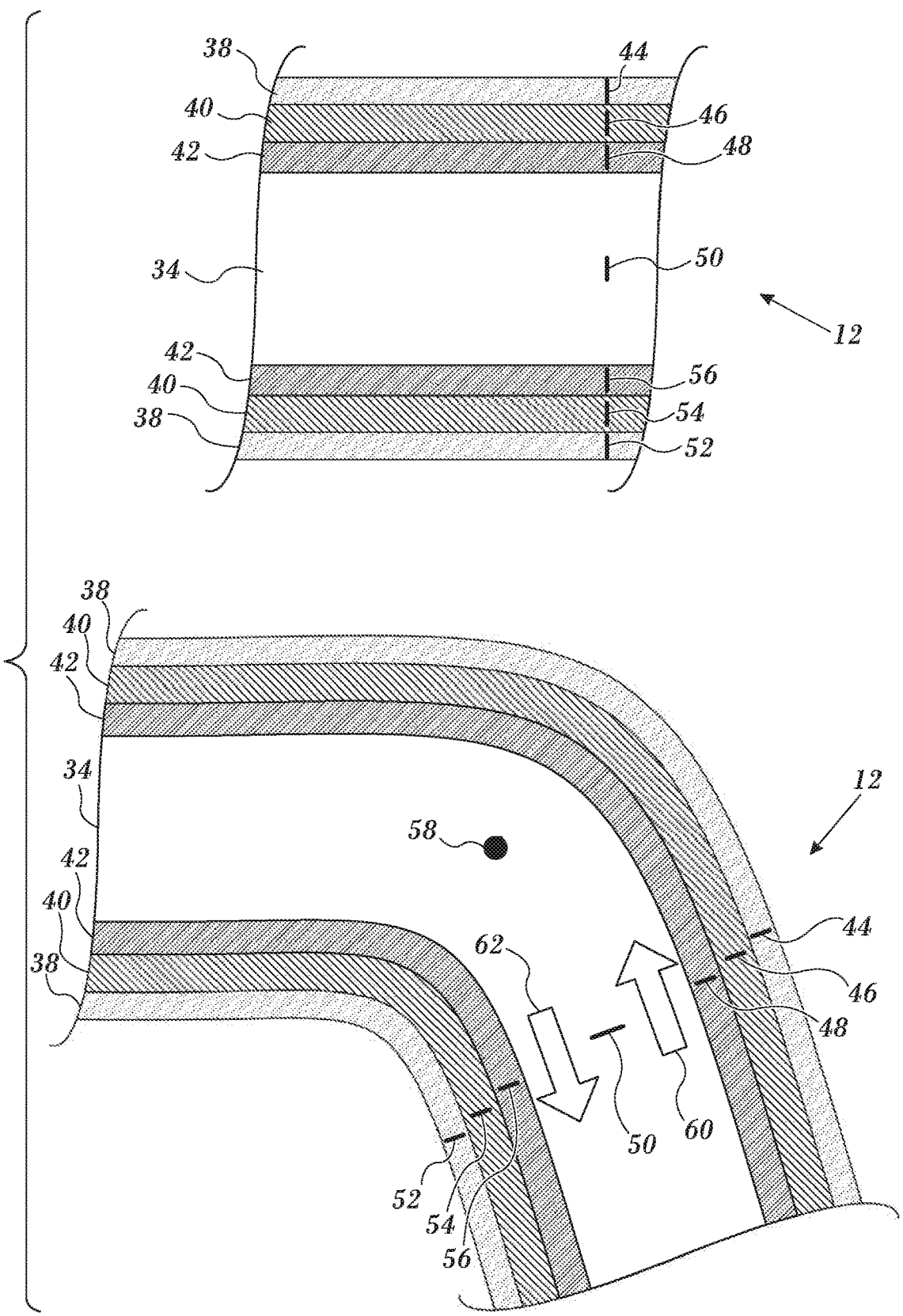
FIG. 3 is a group of two schematic longitudinal sections of portions of the shaft of the catheter shown in FIG. 1 in accordance with an embodiment of the invention.

Reference is now made to FIG. 3, which is are schematic longitudinal sections of portions of the shaft 12 in accordance with an embodiment of the invention. In the upper portion of the figure, the shaft 12 is extended. On one side of the shaft 12 marker 44 in the outer layer 38, marker 46 in middle layer 40 and marker 48 in inner layer 42 are aligned with one another and with reference marker 50 in the inner extrusion 34. On the opposite side of the shaft 12, marker 52 in the outer layer 38, marker 54 in the middle layer 40 and marker 56 in the inner layer 42 are also aligned with reference marker 50.

In the lower portion of the figure the shaft 12 is in a state of flexion at an angle of nearly 90 degrees about a pivot point 58. The markers 44, 46, 48, and markers 52, 54, 56 are no longer in alignment with one another nor with the reference marker 50, because the layers 38, 40, 42 have slid over one another and in the case of inner layer 42, over the inner extrusion 34. At the right side of the shaft 12 the markers 44, 46, 48 are now axially displaced relative to the marker 50, generally toward the pivot point 58 in a direction indicated by arrow 60. The marker 44 in the outer layer 38 has the largest displacement from the reference marker 50, with successively smaller displacements of the markers 46, 48. On the opposite side of the shaft 12, the markers 52, 54, 56 are also displaced relative to the marker 50, but in an opposite direction, generally away from the pivot point 58 as indicated by arrow 62. Marker 52 in the outer layer 38 has the largest displacement from the reference marker 50, with successively smaller displacements of the markers 54, 56.

Of the three layers 38, 40, 42, the layer 38 is under the most compression. The movement of the layers with respect to each other has prevented the shaft 12 from kinking tightly despite the flexion.

Alternate Embodiment

Continuing to refer to FIG. 2 and FIG. 3, in this embodiment the layers 38, 40, 42 are formed on the inner extrusion 34, which is now used as a mandrel by a process of polymer solution casting or film casting, which is known in the art. The same materials used in the first embodiment are suitable, as they possess desired characteristics of lubricity and durometer. Moreover, the layers can be prevented from bonding to one another by film casting an outer layer onto a solidified inner layer.

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

The invention claimed is:

1. A catheter shaft, comprising:
a flexible inner core including a circumference;
a first polymeric layer formed onto the flexible inner core such that the first polymeric layer includes an inner surface that contacts an entirety of the circumference; and
a second polymeric layer formed onto and in contact with the first polymeric layer, wherein upon flexion of the flexible inner core, the first polymeric layer is slidable relative to the flexible inner core and the second polymeric layer, in which the catheter shaft comprises a portion of a medical catheter suitable for inserting into a patient.

2. The catheter shaft according to claim 1, wherein the first polymeric layer and the second polymeric layer are formed by extrusion.

3. The catheter shaft according to claim 1, wherein the first polymeric layer and the second polymeric layer are formed by film casting.

4. The catheter shaft according to claim 1, wherein a kinetic coefficient of friction between the first polymeric layer and the second polymeric layer does not exceed 0.5.

5. The catheter shaft according to claim 1 wherein the first polymeric layer and the second polymeric layer are composed of identical materials.

6. The catheter shaft according to claim 5, wherein the first polymeric layer and the second polymeric layer are composed of polyimide.

7. The catheter shaft according to claim 1 wherein the first polymeric layer and the second polymeric layer are composed of different materials.

8. The catheter shaft according to claim 7, wherein one of the first polymeric layer and the second polymeric layer is ultra-high-molecular-weight polyethylene and another of the first polymeric layer and the second polymeric layer is polyether block amide.

9. The catheter shaft according to claim 1, wherein the flexible inner core comprises a metallic braid.

\* \* \* \* \*